United States Patent [19]

Hansen

[11] Patent Number: 4,464,240
[45] Date of Patent: Aug. 7, 1984

[54] THIODIPROPIONOYL BIS (HALO BENZHYDRAZIDE) ADDITIVES FOR POLYMERS

[75] Inventor: Ralph H. Hansen, Lincoln, Mass.

[73] Assignee: Canusa Coating Systems Limited, Ontario, Canada

[21] Appl. No.: 439,864

[22] Filed: Nov. 8, 1982

[51] Int. Cl.³ .................. C07D 209/52; C08K 5/34
[52] U.S. Cl. ..................... 204/159.2; 174/110 R; 524/94; 548/475
[58] Field of Search ............. 524/94; 548/475; 204/159.2; 174/110

[56] References Cited

U.S. PATENT DOCUMENTS

| | | | |
|---|---|---|---|
| T861,006 | 4/1969 | Tholstrup | 524/192 |
| 3,061,642 | 10/1962 | Weisse et al. | 564/136 |
| 4,087,405 | 5/1978 | Wang et al. | 524/192 |
| 4,178,280 | 12/1979 | Hill | 548/435 |
| 4,189,423 | 2/1980 | Kumano et al. | 524/94 |
| 4,374,220 | 2/1983 | Sonnenberg | 524/94 |

FOREIGN PATENT DOCUMENTS

| | | | |
|---|---|---|---|
| 50-64337 | 5/1975 | Japan | 524/94 |
| 1287934 | 9/1968 | United Kingdom | 524/94 |

Primary Examiner—Veronica P. Hoke
Attorney, Agent, or Firm—Sewall P. Bronstein; Donald Brown

[57] ABSTRACT

Compounds of the formula (I)

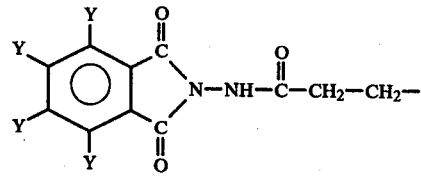

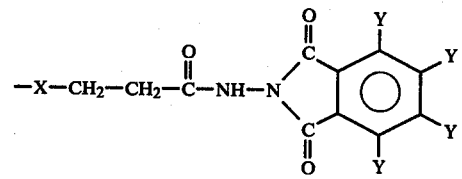

where Y is H, Cl or Br with at least one Y always being Cl or Br and X is S or S—S.

Polymer compositions including antioxidants and the compounds or the compound alone are useful as electrical insulation e.g., for copper cable, as heat shrinkable (heat recoverable) parts or as other plastic parts to improve the retention of mechanical and/or electrical properties of the insulation or parts.

19 Claims, 7 Drawing Figures

THIODIPROPIONOYL BIS (HALO BENZHYDRAZIDE) ADDITIVES FOR POLYMERS

BRIEF STATEMENT OF THE INVENTION

This invention is directed to a compound of the formula (I)

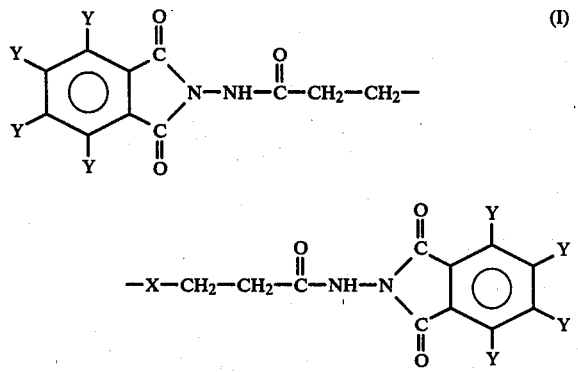

where Y is H, Cl or Br with at least one Y always being Cl or Br and X is S or S—S most preferably each Y is Br or each Y is Cl and X is S, and its use in polymers as a flame retardant as well as a synergist for antioxidants used in such polymers or as an antioxidant or flame retardant in its own right, and articles of manufacture made comprising polymers with the compound.

While it would be expected that the compounds (I) would have nil antioxidant properties at elevated temperatures in a polymer unexpectedly the compounds of formula (I) have antioxidant properties comparable to compounds which would be considered to be primary antioxidants. The compounds will also, when used in combination with one or more primary antioxidants will substantially and unexpectedly increase the useful life of the polymer at elevated temperatures without requiring the high loading of the primary antioxidants (also referred to as chain breaking antioxidants).

While it may be possible to use additional antioxidants, to achieve the increased polymer life at elevated temperatures, primary antioxidants commonly used tend to diffuse out of the polymer at high concentrations and form undesirable coating (termed blooming) on the surface thereof. In addition, the loss of primary antioxidant will over a period of time permit oxidation to take place at an accelerated rate and thereby significantly decrease the mechanical and electrical properties of the polymer thus shortening its lifetime. The commonly used antioxidant synergist (synergists are sometimes referred to as secondary antioxidants, and also referred to as peroxide decomposing antioxidants) DLTDP (dilauryl thiodipropionate) also is known to bloom.

The present invention is useful in polymers used for electrical insulation, in heat shrinkable tubing and other parts, e.g., end caps made of polyethylene and used for electrical purposes, as well as in other plastic (polymer) parts used as utensils or as parts of the tubs of washing machines to prevent them from becoming brittle due to loss of antioxidant (because of soapy water causing the antioxidants commonly used to leach out of the plastic).

The compounds of formula (I) are particularly useful in heat recoverable (heat shrinkable) articles of manufacture such as tubing, end caps and other hollow articles to which heat is applied to cause shrinkage because the lack of blooming permits cooling with adhesives which may contain metal particles.

Polymers in which the compound of formula (I) are useful in this invention include all thermoplastics and thermohardening (thermosetting) plastics in which antioxidants are employed. Suitable plastics may include polyolefins such polyethylene (high and low density), polypropylene, polybutylene, substituted polyolefins such as halogenated olefin polymers and copolymers of same and silane grafted polyethylenes, e.g., grafted using a silane such as vinyl trimethoxy silane as the grafting agent, (see U.S. Pat. No. 3,086,242).

The compounds of formula (I) would also be useful with any polymer whose useful properties are adversely affected by oxidative degradation such as esters, amides (e.g., nylon), phenolics, acrylics, rubber, urethanes, vinyls, styrenes (e.g. ABS), and others used in the plastics industry. See the Test PLASTICS IN THE MODERN WORLD by E. G. Couzens and V. E. Yarsly (C) 1968, published by Pelican Books, Inc., Maryland U.S.A., for other polymers used in industry and useful in this invention.

Prior art patents showing heat recoverable plastics and articles include U.S. Pat. Nos. 4,048,129, 4,016,356, 3,982,546 and 3,959,052. It should be understood that heat recoverable articles are meant to include those that are treated by irradiation or chemically treated to produce such articles.

Examples of primary antioxidants useful in a polymer with the compounds of formula (I) include:

| ANTIOXIDANTS | |
|---|---|
| Commercial Name | Chemical Name |
| Irganox 1010 | tetrakis[methylene-3(3',5'-di-tert-butyl-4'-hydroxyphenyl)propionate]methane |
| Santonox R | 4,4'-thiobis(3-methyl-6-tert-butyl phenol) |
| Irganox 1024 | N,N'—-bis(3,5-di-tert-butyl-4-hydroxy-hydrocinnamoyl) hydrazine |
| Cyanox 1729 | Bis(4-tert-butyl-3-hydroxy-2,6-dimethyl benzyl) dithiolterephthalate |
| Ethyl 330 | 1,3,5,Trimethyl-2,4,6,-tris[3,5 di-tert-butyl-4 hydroxy benzyl]-benzene |
| Agerite White | di-β-napthyl-p-phenylene-diamine |
| Irganox 1035 | thiodiethylene bis(3,5-di-tert-butyl-4-hydroxy) hydrocinnamate |

Other suitable commercial antioxidants include Good-Rite 3114, Plastanox 2246, Naugard 449, Naugard XL-1, Irganox 1093, Irganox 1076, Topanol CA, and Irganox 565. Other antioxidants (normally termed primary antioxidants) in the art may be found in the text ANTIOXIDANTS, RECENT DEVELOPMENTS, CHEMICAL TECHNOLOGY REVIEW NO. 127, by M. William Ronney, Noyes Data Corporation (C) 1979, Library of Congress, Catalog No. 79-84425.

In using thus invention to form polymeric articles, while the compounds of formula (I) acts as a synergist, it is preferred that an amount of the compound of formula (I) to the amount of antioxidant is in the ratio of 1:10 to 10:1 with the total weight of antioxidant and the compounds of formula (I) being within the range of 0.05 to 150% (generally 50 to 100%) based on the weight of the polymer (resin) with 0.05 to 10% being the preferred range where it is used solely for its antioxidant properties.

The compounds of formula (I) provide the sulfur for synergism with primary (strong) antioxidants (see list of antioxidants on previous page) and also includes halogen atoms.

In using the compounds of formula (I) by themselves as antioxidants in a polymer, the concentration used should preferably be between 0.05 to 10% of the weight of the polymer depending upon environmental conditions to be met. When the compounds of Formula I are to be used as flame retardants as well, the preferred concentrations can be as high as 150% of the weight of the polymer.

In FIGS. 1 to 7 there are shown various forms of the invention. FIGS. 1 to 5 illustrate hollow articles as does FIG. 7.

FIGS. 1, 2 and 3 illustrate a tube 20 formed of material such as polyethylene and containing an antioxidant and a compound of formula (I) or a compound of formula (I) alone. The tube is formed by conventional technology to be heat shrinkable e.g., see U.S. Pat. Nos. 3,086,242 and 3,303,243. See U.K. Patent Application No. 1,601,063 published Oct. 21, 1981 for an illustration of chemically produced heat shrinkable material. Conventional cross-linked silane grafted polyethylene as shown in U.S. Pat. No. 3,086,242. The material of U.S. Pat. No. 3,086,242 will be modified by the incorporation of antioxidant and a compound of formula (I) as disclosed herein.

The tube 20 is shrunk as shown in FIG. 3 over electrical cable 21 to provide an insulative protective cover which will protect against moisture and other deleterious substances.

FIGS. 2 and 5 illustrate a heat recoverable end cap 25 (a closed at one end hollow article) with FIG. 5 showing the end cap 25 shrunk over a pair of wires 26 and 27. The end cap 25 is made by using the polymer material of the invention in a manner well known in the art.

FIGS. 6 and 7 show a sheet 30 of material of the invention rolled over upon itself as in FIG. 7 to form a tube. The sheet may be heat recoverable or not depending upon the desires of the end use. A heat recoverable sheet may be made by methods known in the art.

In this invention, the preferred primary antioxidants are those characterized in the art as hindered phenolics or aromatic amines.

Figure 1:
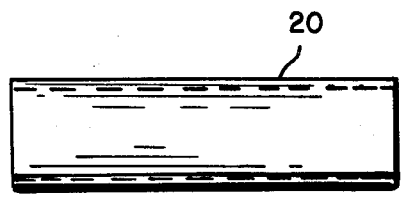
FIG. 1 is a side view of a tube.
Figure 2:
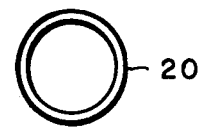
FIG. 2 is an end view of a tube.
Figure 3:
FIG. 3 is a sectional view of the tube of FIGS. 1 and 2 shrunk over wire or cable.
Figure 4:
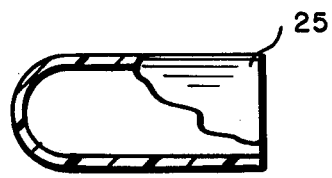
FIG. 4 is a sectional view of an end cap.
Figure 6:
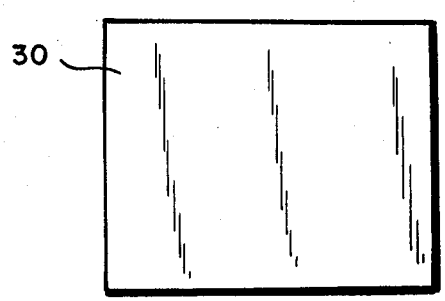
FIG. 6 is a top view of a sheet of polymer material of the invention.
Figure 5:
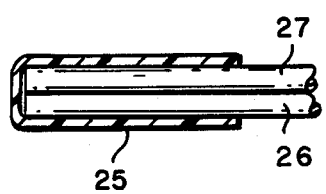
FIG. 5 is a sectional view of the end cap of FIG. 4 shrunk over a pair of wires.
Figure 7:
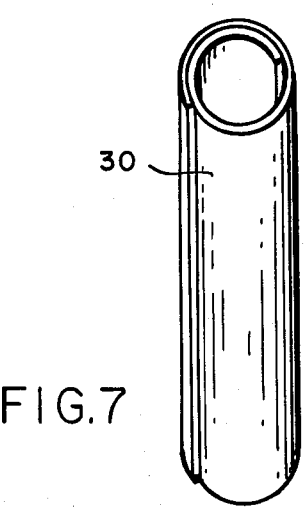
FIG. 7 is a perspective view of the sheet of FIG. 6 rolled up upon itself to form a tube.

The following examples are illustrative of the practice of the invention and are not intended for purposes of limitation. All parts are by weight and all temperatures are in centigrade.

EXAMPLE 1

Preparation of the compound of formula (I) where X is S and each Y is Br

The compound of this example may be prepared in two steps as follows: Sixty ml. of water is heated to about 60° C. and 10 grams of dimethyl thiodipropionate

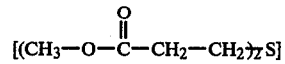

are added with stirring.

To this two-phase composition is added 7.3 grams of hydrazine hydrate [NH$_2$NH$_2$]H$_2$O (a 50% excess) while stirring is continued. In about 5 minutes the suspension clarifies and reaction appears to be complete. Stirring is continued for an additional 25 minutes and the solution is cooled to about 5° C. (crystals form at about 35° to 40° C.), filtered and dried. The yield is about 7.5 grams of thiodipropionic acid dihydrazide, m.p. 154° C. (Perkin-Elmer DSC-2 calorimeter at a heating rate of 10°/minute). The yield may be increased by re-using the mother liquor in place of the water, by concentrating the mother liquor, or by diluting with a poor solvent for the dihydrazide such as methanol.

The thiodipropionic acid hydrazide

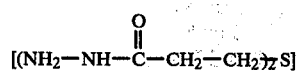

is used without further purification. To 300 ml. of water at room temperature is added 10 grams of powered tetrabromophthalic onhydride and 10 grams of the thiopropionic dihydrozide. The mixture is stirred at room temperature for 1 hour and then the temperature is raised to approximately 100° C. over a two-hour period. The solid is filtered, washed with water and dried. A nearly quantitative yield (19 grams) compound of formula (I) is obtained.

This ditetrabromo compound (where each Y is Br and X is S) endotherm at about 165° C. (Perkin-Elmer DSC-2 calorimeter at a heating rate of 10° C./minute). It is substantially white and is insoluble in boiling water.

EXAMPLE 2

Using the compound of Example 1 a number of compositions are prepared by mixing the proportions of ingredients (percent by weight shown) into a polymer comprising 9% vinyl acetate—91% ethylene copolymer (commercially known as U.S. Industrial Chemicals UE 635) on a heated, two-roll mill, molding into a sheet approximately 75 mils thick as shown below:
(i) 0.5 part by weight of Naugard XL-1 [2,2'-oxamidobis ethyl 3 (3,5-ditert-butyl-4-hydroxyphenyl) propionate] and 3 parts by weight compound of Example 1 and 100 parts by weight of the polymer;
(ii) 3 parts by weight of the compound of Example 1 and 100 parts by weight of the polymer; and
(iii) 1 part by weight of the compound of Example 1 and 100 parts by weight of the polymer.

EXAMPLE 3

Preparation of the compound of formula (I) where X equals S—S and each Y is Br

The dibenzal derivative of the dihydrazide of thiodipropionic acid (compound of formula (I) may be prepared in two steps as follows: Sixty ml. of water is heated to about 60° C. and 11.6 grams of dimethyl dithiodipropionate

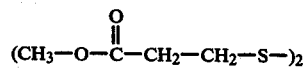

are added with stirring.

To this two-phase composition is added 7.4 grams of hydrazine hydrate [NH₂NH₂]H₂O (a 50% excess) while stirring is continued. In about 5 minutes the suspension clarifies and reaction appears to be complete. Stirring is continued for an additional 25 minutes and the solution is cooled to about 5° C. (crystals form at about 35° to 40° C.), filtered and dried. The yield is about 8.5 grams of thiodipropionic acid dihydrazide. The yield may be increased by re-using the mother liquor in place of the water, by concentrating the mother liquor, or by diluting with a poor solvent for the dihydrazide such as methanol.

The dithiodipropionic acid hydrazide

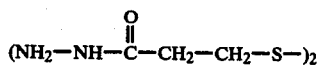

is used without further purification. To 300 ml. of water at room temperature is added 10 grams of tetrabromo phthalic anhydride and 11.6 grams of the dithiodipropionic dihydrazide, with stirring. After one hour the temperature is raised to approximately 100° C. over a two-hour period. The solid is filtered, washed with water, and dried.

A nearly quantitative yield (19.5 grams) of the compound of formula (I) is obtained. It is substantially white and is insoluble in boiling water. CL EXAMPLE 4

Using the compound of Example 3 a number of compositions are prepared by mixing the proportions of ingredients (percent by weight shown) into a polymer comprising 9% vinyl acetate—91% ethylene copolymer (commercially known as U.S. Industrial Chemicals UE 635) on a heated, two-roll mill, molding into a sheet approximately 75 mils thick as shown below:

(i) 0.5 part by weight of Naugard XL-1 [2,2′-oxamidobis ethyl, 3 (3,5-di-tert-butyl-4-hydroxyphenyl) propionate] and 3 parts by weight compound of Example 3 and 100 parts by weight of the polymer;

(ii) 3 parts by weight of compound of Example 3 and 100 parts by weight of the polymer; and (iii) 1 part by weight of the compound of Example 3 and 100 parts by weight of the polymer.

Examples of commercially available materials from which compounds of Formula (I) are preparable include 4-chlorophthalic acid and 4, 5-dichlorophthalic acid.

I claim:

1. A compound of the formula (I)

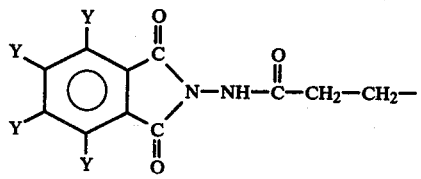

(I)

-continued

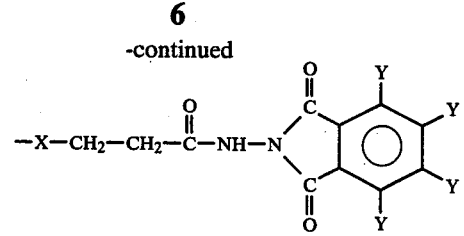

where X is S or S—S and Y is H, Cl or Br with at least one Y always being Cl or Br.

2. The compound of claim 1 in which X is S and each Y is Br.

3. The compound of claim 1 in which X is S and each Y is Cl.

4. A composition comprising a polymer and the compound of claim 1 in an amount sufficient to impart flame retardant and antioxidant properties.

5. The composition of claim 4 in which the polymer is polyethylene or polypropylene.

6. The composition of claim 4 in which the amount of the compound of formula (I) comprises 0.05 to 150% based on the weight of the polymer.

7. As an article of manufacture, an electrical conductor and a layer of insulation about said conducter comprising the composition of claim 4.

8. The article of claim 7 in which X is S or S—S and each Y is Br.

9. The composition of claim 2 containing an additional antioxidant.

10. The composition of claim 9 in which the ratio of a compound of formula to the antioxidant is 1:10 to 10:1 and the amount of the antioxidant and a compound of formula (I) is 0.05% to 10% based on the weight of the polymer.

11. The composition of claim 9 in which the additional antioxidant is a hindered phenolic or an aromatic amine.

12. The composition of claim 1 which includes 0.05% to 150% of the compound based on the weight of the polymer.

13. The composition of claim 12 in which X is S and each Y is Br.

14. The composition according to claim 13 in which in which the compound is 50% to 100%.

15. As an article of manufacturer, a heat recoverable article comprising a polymer and the compound of formula (1)

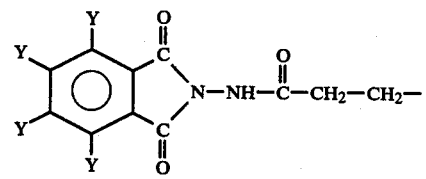

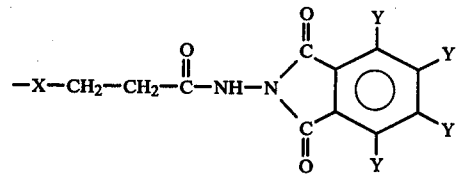

where X is S or S—S and Y is H, Cl or Br provided that at least one Y is always Cl or Br, in an amount sufficient to impart flame retardant and antioxidant properties in the presence or absence of an additional antioxidant.

16. The article of claim 15 in which the polymer is a polyolefin.

17. The article of claim 6 in which the polyethylene is cross-linked with silane or by irradiation.

18. The article of claim 11 in which the silane is vinyl trimethoxysilane.

19. The article of claim 15 in the form of a hollow tube and member.

* * * * *